United States Patent [19]

Alsobrook

[11] Patent Number: 4,971,204

[45] Date of Patent: Nov. 20, 1990

[54] CATHETER HANGER

[76] Inventor: Harold D. Alsobrook, Rte. 4, Box 1108, Tyler, Tex. 75703

[21] Appl. No.: 14,972

[22] Filed: Feb. 17, 1987

[51] Int. Cl.⁵ .................................................. A47F 7/00
[52] U.S. Cl. ........................................ 211/13; 211/58; 211/205
[58] Field of Search ............... 211/57.1, 58, 60.1, 211/70, 163, 166, 13, 205

[56] References Cited

U.S. PATENT DOCUMENTS

| | | | |
|---|---|---|---|
| 591,453 | 10/1897 | Chickering | 211/163 X |
| 1,141,274 | 6/1915 | Skall | 211/58 X |
| 1,221,517 | 4/1917 | Dunbar | 211/70 |
| 1,697,866 | 1/1929 | Hansen | 211/163 X |
| 1,729,004 | 9/1929 | Miadowicz | 211/166 |
| 2,639,820 | 5/1953 | Lee | 211/163 |
| 3,734,301 | 5/1973 | Rastocny | 211/165 X |
| 4,526,335 | 7/1985 | Garfinkle | 211/57.1 X |
| 4,645,081 | 2/1987 | Korth | 211/166 X |

Primary Examiner—Ramon O. Ramirez

[57] ABSTRACT

In a medical supply room, packaged catheters are hung upon a rack for ready access. The rack has six arms radiating from a rotatable hub. The catheters are hung upon rods which extend across each of the arms.

6 Claims, 1 Drawing Sheet

CATHETER HANGER

RIGHTS TO INVENTIONS UNDER FEDERAL RESEARCH

There was no federally sponsored research and development concerning this invention.

BACKGROUND OF THE INVENTION (1) Field of the Invention

This invention relates to storage of medical supplies and more particularly to a rack for holding packaged catheters.

(2) Description of the Related Art

Catheters come in many different configurations and construction as well as different length. Typically, each catheter is separately packaged. Each package will be about 48" long and about 3" wide. Many of the packages will be longer or shorter and may vary in width. Normally the package is only a fraction of an inch in thickness, the thickness depending upon the diameter of the catheter contained therein. Also, typically, the catheter package will have a hanging hole at the top thereof.

A medical laboratory supply room will often have more than 1,000 catheters therein.

Most of the catheters which will be used are described as heart catheters inasmuch as they have a terminal end with the tip within or near the heart.

Typically, before this invention, packages of catheters were hung on rods or pegs extending from a pegboard attached to a wall of a laboratory or supply room. It will be understood that the wall space of laboratories or supply rooms is often quite limited since it is necessary to have filing cases or equipment or supply shelves or other supply containers in the available space which is often is adjacent to the walls. Therefore, it was not uncommon to have several packages of catheters hanging from a single peg.

It will be understood that this method of storage was not satisfactory As stated before, valuable wall space was used for storing the catheters, it was difficult to inventory the catheters, and also it was difficult to locate a catheter when needed. It will be understood that often catheters are used in medical emergencies, and the difficulty or time consumed in trying to find the proper catheter is sometimes critical. In any event, the person in charge of the medical supplies is normally a highly skilled person, and even in the least busy times it is well not to waste time of the supply room personnel.

Before this application was filed, the applicant caused a search to be made in the U.S. Patent and Trademark Office. The following patents were found on that search:

| | |
|---|---|
| BRADY | 274,457 |
| MIADOWICZ | 1,729,004 |
| HANSEN | 1,697,866 |
| TURNBULL | 2,334,518 |
| RASTOCNY | 3,734,301 |

TURNBULL discloses a rotary clothesline.
BRADY discloses a nursery towel rack.
RASTOCNY, MIADOWICZ, and HANSEN each disclose display devices.

These patents are considered pertinent because the applicant believes the Examiner would consider anything revealed by an experienced patent searcher to be relevant and pertinent to the examination of this application.

SUMMARY OF THE INVENTION (1) Progressive Contribution to the Art

I have invented a rack for storing packages of medical catheters.

I have discovered a more efficient way to store catheter packages so that the catheter packages may be readily located and also require less storage space. This is done by storing the catheters upon rods which extend from struts which radiate from a rotable hub. The hub is supported by a column extending upward from a pedestal.

(2) Objects of this Invention

An object of this invention is to store packages of medical catheters.

Further objects are to achieve the above with devices that provide compact, economical, space saving, dust free environment for the catheter storage, and where the catheters are easily identifiable, and the devices are sturdy, durable, lightweight, simple, safe, efficient, versatile, ecologically compatible, energy conserving, and reliable, yet inexpensive and easy to manufacture, connect, adjust, and maintain.

The specific nature of the invention, as well as other objects, uses, and advantages thereof, will clearly appear from the following description and from the accompanying drawing, the different views of which are not scale drawings.

Figure 1:
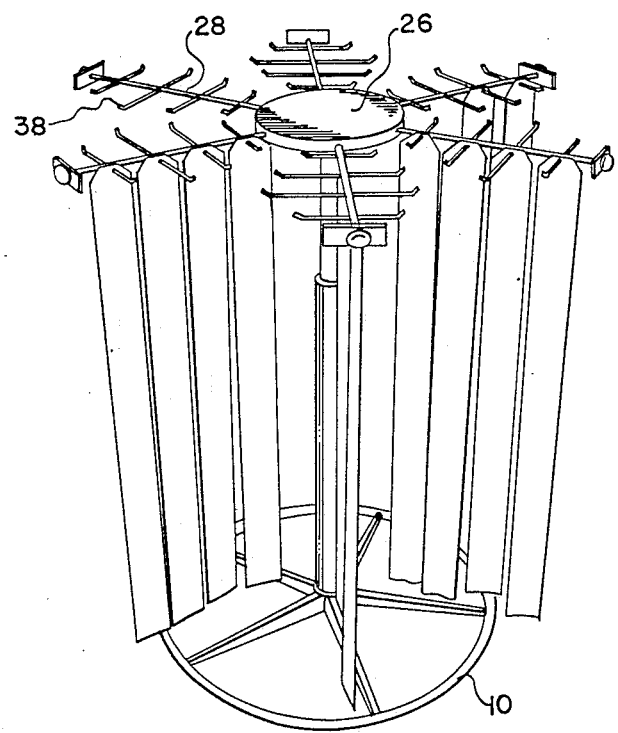
FIG. 1 is a perspective view of a hanger according to this invention showing a few catheter packages hanging thereon.
Figure 2:
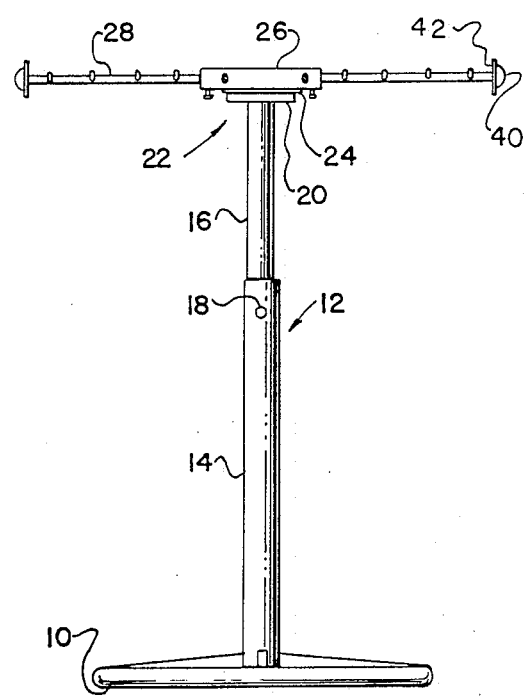
FIG. 2 is a side elevational view of a hanger without packages with some of the struts removed for clarity of illustration.
Figure 3:
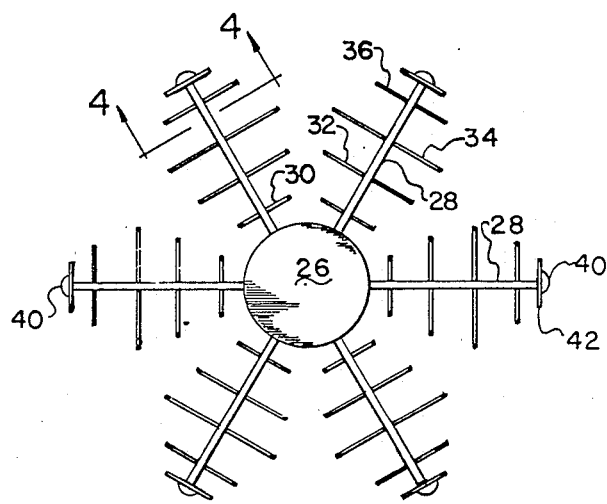
FIG. 3 is a top plan view without the pedestal for clarity of illustration.
Figure 4:
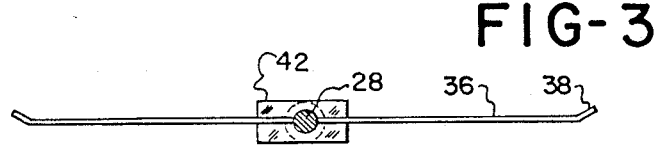
FIG. 4 is a detailed view of one rod on one strut taken substantially on line 4—4 of FIG. 3.

As an aid to correlating the terms of the claims to the exemplary drawing, the following catalog of elements is provided:

| | |
|---|---|
| 10 | pedestal |
| 12 | column |
| 14 | lower section |
| 16 | upper section |
| 18 | clamp means |
| 20 | bottom portion |
| 22 | turntable |
| 24 | upper portion |
| 26 | hub |
| 28 | struts |
| 30 | first rod |
| 32 | second rod |
| 34 | third rod |
| 36 | fourth rod |
| 38 | tips |
| 40 | handle |
| 42 | label |

DESCRIPTION OF THE PREFERRED EMBODIMENT

Referring to the drawings, there may be seen a rack or hanger wherein column 12 rises from the pedestal being attached thereto. The column h's two sections, lower section 14 with upper section 16 telescoped therein. Clamp means 18 on the top of the lower, outer section 14 is in the form of a set screw. It forms means for securely attaching the two sections of the column 12 into an adjusted position.

The bottom portion 20 of turntable 22 is attached to the top of column 12, which would be the top of the upper section 16. The upper portion 24 of the turntable 22 is securely attached to the bottom of hub 26. The turntable has ball bearings.

It will be understood that the turntable 22 forms a means for allowing the hub 26 to be rotated relative to the column 12 Also, it will be apparent that if the hub 26 may be rotated relative to the column 12 it is also rotated relative to the pedestal 10.

A plurality of arms or struts 28, specifically six, radiate from the hub 26. The struts 28 are horizontal and evenly spaced about the hub. The struts 28 are all of the same length. Four hanger rods are attached to each strut 28. The rods are designated as first rod 30, second rod 32, third rod 34, and fourth rod 36. Referring to the drawing, the first rod 30 is proximal of the hub 26; and therefore, will be referred to as the proximal rod. The fourth rod 36 is near the distal end of the strut 28; and therefore, will be referred to as the distal rod. The hanger rods 30–36 are all horizontally oriented and at right angles normal to the strut 28. Each of the rods extends for an equal distance on each side of the strut. Tip 38 on each distal end of each rod angles upward so that catheter packages hung on the rod are retained thereon in normal usage. When it is desired to remove a catheter from the rod, they may be readily removed from the rod and likewise, they are readily placed upon the rod when replenishing the supply of catheters on the rack or hanger.

The first rod 30 is the shortest of all the rods. The length of the first rod is such that so that the tips 38 of the first rod 30 is separated from the tip of the first rod 30 on the adjacent strut 28, a sufficient distance so that the catheters can be easily placed upon and removed from the rods 30. The second rod 32 is longer than the first rod 30, which is to say that the first rod 30 is shorter than the second rod 32. The distance between the tips of the second rods 32 on adjacent struts 28 is sufficient so that there is access to the first rods 30. There is more distance between the tips of the second rod 32 than there is between the tips of the first rods 30. The term "distance between the tips" in this specification refers to the distance between the tip of a rod on one strut and the tip of a rod on the adjacent strut.

Likewise, the distance between the tips of the third rods 34 is greater than the distance between the tips of the first rods 30 or the second rods 32. By having the distance between the tips of the third rods 34 greater than the distance between the inner arms, access can always be had to the inner arms. The distance between the tips of the distal rods 36 is greater than the distance between any of the other tips. Therefore, as stated before, there is always adequate access to the catheters upon the inner rods.

Handle 40 provides a convenient hand hold on the distal end of each of the struts 28. The personnel in the laboratory may readily hold the array of struts and rods in a steady position by placing one hand on the handle 40 while removing or replacing catheter packages upon any of the hanger rods.

Label 42 in the form of a plastic plate provides a surface upon which indices may be placed indicating the catheters upon the rods of that arm. This label is located on the struts 28 between the handle 40 and the distal rod 36. Therefore, the label is distal of the fourth rod 36 and near the handle 40.

I prefer the hub to be about 60" above the floor and the distance from handle 40 on one strut 28 to handle 40 on the opposite strut to be about 52". In such a situation, the pedestal 10 would have a diameter of less than 52". It is desirable that the pedestal have sufficient diameter to provide a stable base for the holder or rack. It may be readily seen that with this arrangement there are a total of 48 pegs or half rods extending upon which to place catheters. These 48 are arranged with eight half rods on either side of a bay, the bay being the open space between adjacent struts. Although ordinarily only similar type catheters or catheters length will be placed on any given half bay, this is not essential. I.e., catheters of different types may be placed upon the same strut. The label at the end of each strut is useful in helping the personnel find the right catheter as needed. Also, by having numerous places to put the catheters, they may be easily inventoried for reordering.

The embodiment shown and described above is only exemplary. I do not claim to have invented all the parts, elements or steps described. Various modifications can be made in the construction, material, arrangement, and operation, and still be within the scope of my invention. For example, I prefer that the column be made of aluminum alloy and the arms of tubing and hub of aluminum. Also, I prefer that the entire rack be chrome plated so that it is more acceptable in medical surroundings such as a hospital.

The restrictive description and drawing of the specific examples above do not point out what an infringement of this patent would be, but are to enable one skilled in the art to make and use the invention. The limits of the invention and the bounds of the patent protection are measured by and defined in the following claims.

I claim as my invention:

1. A rack for hanging medical catheter packages comprising:
    a. a pedestal,
    b. a column attached to the pedestal,
    c. a turntable on the top of the column,
    d. a hub attached to the top of the turntable,
    e. said turntable forming a means on the top of the column for allowing the hub to be rotated relative to the column and the pedestal,
    f. six horizontal struts radiating from the hub,
    g. four hanger rods attached to each strut, the rods designated as first, second, third, and fourth rod, with the first rod being the proximal rod and the fourth rod being the distal rod,
    h. said hanger rods extending horizontally at right angles to the strut, and an equal distance on each side of the strut, and
    i. a tip at each distal end of each rod angled upward so that catheter packages hung on the rod are retained thereon,
    j. the first rod is shorter than the second rod, and the second rod is shorter than the third rod, and the third rod is longer than the fourth rod, so that there is adequate distance between the tip of the first rod on one strut and the tip of the first rod on adjacent struts, this distance being adequate for hanging and removing catheter packages on the first rods, k. there being more distance between the tips of second rods on adjacent struts than there are between first rods on adjacent struts so that there is access to the first rods, there being more distance between the tips of third rods on adjacent struts than there are between the tips of second rods on adjacent struts so that there is access to the second rods and the first rods.

2. The invention as defined in claim 1 wherein:
l. said column has two sections, a lower section and an upper section,
m. one of the said sections being telescoped within the other,
n. clamp means on one of the sections for securely attaching the sections together in an adjustable position.

3. The invention as defined in claim 1 further comprising:
a label distal of the fourth rod on each of the struts.

4. The invention as defined in claim 1 further comprising:
a handle at the distal end of each strut.

5. The invention as defined in claim 4 further comprising:
m. a label distal of the fourth rod on each of the struts.

6. A rack for hanging medical catheter packages comprising:
a. a pedestal,
b. a column attached to the pedestal,
c. a turntable on the top of the column,
d. a hub attached to the top of the turntable,
e. said turntable forming a means on the top of the column for allowing the hub to be rotated relative to the column and the pedestal,
f. six horizontal struts radiating from the hub,
g. four hanger rods attached to each strut, the rods designated as first, second, third, and fourth rod, with the first rod being the proximal rod and the fourth rod being the distal rod,
h. said hanger rods extending horizontally at right angles to the strut, and an equal distance on each side of the strut, and
i. a tip at each distal end of each rod angled upward so that catheter packages hung on the rod are retained thereon,
j. the first rod is shorter than the second rod, and the second rod is shorter than the third rod, and the third rod is longer than the fourth rod, so that there is adequate distance between the tip of the first rod on one strut and the tip of the first rod on adjacent struts, this distance being adequate for hanging and removing catheter packages on the first rods,
k. there being more distance between the tips of second rods on adjacent struts than there are between first rods on adjacent struts so that there is access to the first rods, there being more distance between the tips of third rods on adjacent struts than there are between the tips of second rods on adjacent struts so that there is access to the second rods and the first rods,
l. a handle at the distal end of each strut,
m. a label distal of the fourth rod on each of the struts,
n. said column has two sections, a lower section and an upper section,
o. one of the said sections being telescoped within the other,
p. clamp means on one of the sections for securely attaching the sections together in an adjustable position.

* * * * *